United States Patent
Burkett et al.

(10) Patent No.: US 11,219,748 B2
(45) Date of Patent: Jan. 11, 2022

(54) INTRAVASCULAR DEVICES, SYSTEMS, AND METHODS HAVING A POLYMER JACKET FORMED AROUND COMMUNICATION LINES WRAPPED AROUND A CORE MEMBER

(71) Applicant: Koninklijke Philips N.V., Amsterdam (NL)

(72) Inventors: David Burkett, Temecula, CA (US); Eric Henderson, Temecula, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 15/098,012

(22) Filed: Apr. 13, 2016

(65) Prior Publication Data
US 2016/0303354 A1 Oct. 20, 2016

Related U.S. Application Data
(60) Provisional application No. 62/147,283, filed on Apr. 14, 2015.

(51) Int. Cl.
| | |
|---|---|
| *A61M 25/09* | (2006.01) |
| *A61B 5/0215* | (2006.01) |
| *A61B 5/026* | (2006.01) |
| *A61B 8/00* | (2006.01) |
| *A61B 5/00* | (2006.01) |
| *A61B 5/03* | (2006.01) |

(52) U.S. Cl.
CPC ............. *A61M 25/09* (2013.01); *A61B 5/026* (2013.01); *A61B 5/0215* (2013.01); *A61B 5/6851* (2013.01); *A61B 8/4444* (2013.01); *A61B 5/036* (2013.01); *A61M 2025/09166* (2013.01)

(58) Field of Classification Search
CPC ........ A61M 25/09; A61M 2025/09166; A61B 5/6851; A61B 5/0215; A61B 5/026; A61B 8/4444; A61B 5/036
USPC .................................................. 600/437–480
See application file for complete search history.

(56) References Cited

U.S. PATENT DOCUMENTS

| | | | |
|---|---|---|---|
| 5,095,915 A | | 3/1992 | Engelson |
| 5,243,988 A | * | 9/1993 | Sieben ..................... A61B 8/12 128/925 |
| 5,333,620 A | | 8/1994 | Moutafis |
| (Continued) | | | |

FOREIGN PATENT DOCUMENTS
EP 1849409 A1 10/2007

*Primary Examiner* — Sanjay Cattungal

(57) ABSTRACT

Intravascular devices, systems, and methods are disclosed. In some instances, the intravascular device is a guide wire having a polymer jacket applied over communication lines and a core member, where the communication lines have been wrapped around the core member. For example, in some implementations a sensing guide wire includes a proximal portion and a distal portion, the distal portion including: a core member; a plurality of communication lines wrapped around the core member; a polymer jacket formed around the core member and the plurality of communication lines; and a sensing element positioned distal of the polymer jacket and communicatively coupled to the plurality of communication lines. Methods of making, manufacturing, and/or assembling such intravascular devices and associated systems are also provided.

22 Claims, 16 Drawing Sheets

(56) References Cited

U.S. PATENT DOCUMENTS

| | | | |
|---|---|---|---|
| 5,353,798 A * | 10/1994 | Sieben | A61B 8/12 128/925 |
| 5,746,701 A | 5/1998 | Noone | |
| 5,827,201 A | 10/1998 | Samson | |
| 6,419,745 B1 | 7/2002 | Burkett | |
| 6,908,443 B2 * | 6/2005 | Burmeister | A61M 25/09 600/585 |
| 8,968,331 B1 | 3/2015 | Sochor | A61N 1/0534 606/129 |
| 2001/0009980 A1 | 7/2001 | Richardson | |
| 2003/0019661 A1 * | 1/2003 | Aoyama | H01B 1/026 174/126.1 |
| 2003/0114777 A1 * | 6/2003 | Griffin | A61L 31/022 600/585 |
| 2004/0153006 A1 | 8/2004 | Vrba | |
| 2004/0167439 A1 | 8/2004 | Sharrow | |
| 2005/0065434 A1 | 3/2005 | Bavaro | |
| 2005/0124917 A1 | 6/2005 | Skujins | |
| 2006/0085054 A1 * | 4/2006 | Zikorus | A61B 18/08 607/96 |
| 2008/0132806 A1 | 6/2008 | Smith | |
| 2010/0063478 A1 * | 3/2010 | Selkee | A61B 5/042 604/524 |
| 2010/0228112 A1 * | 9/2010 | Von Malmborg | A61B 5/0215 600/373 |
| 2011/0220389 A1 * | 9/2011 | Huang | H01B 11/203 174/113 R |
| 2012/0116382 A1 * | 5/2012 | Ku | A61B 18/1492 606/33 |
| 2014/0132267 A1 * | 5/2014 | Wedan | G01R 33/288 324/318 |
| 2014/0142398 A1 * | 5/2014 | Patil | A61B 6/463 600/301 |
| 2014/0187874 A1 * | 7/2014 | Burkett | A61B 5/0215 600/301 |
| 2014/0187960 A1 * | 7/2014 | Corl | A61B 8/12 600/466 |
| 2014/0187982 A1 * | 7/2014 | Millett | A61B 5/0215 600/486 |
| 2014/0276223 A1 * | 9/2014 | Gustafsson | A61B 5/6851 600/585 |
| 2015/0272449 A1 * | 10/2015 | Meyer | A61B 5/0215 600/424 |
| 2015/0272654 A1 * | 10/2015 | Esch | A61B 18/082 606/34 |
| 2019/0330055 A1 * | 10/2019 | Millett | A61B 5/0215 |

* cited by examiner

INTRAVASCULAR DEVICES, SYSTEMS, AND METHODS HAVING A POLYMER JACKET FORMED AROUND COMMUNICATION LINES WRAPPED AROUND A CORE MEMBER

CROSS-REFERENCE TO RELATED APPLICATIONS

The present application claims priority to and the benefit of U.S. Provisional Patent Application No. 62/147,283, filed Apr. 14, 2015, which is hereby incorporated by reference in its entirety.

TECHNICAL FIELD

The present disclosure relates to intravascular devices, systems, and methods. In some embodiments, the intravascular devices are guide wires that include one or more electronic, optical, or electro-optical components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire.

Guide wires are designed to be steered through vascular anatomy to suspected lesion sites to allow for treatment of those lesions. There are many desired performance characteristics that have to be considered for the guide wire design: torqueability, support level, tip stiffness, lubricity, smooth transitions, and device compatibility. Regardless of the design needs, good torqueability of the wire tip remains the most important performance output of the wire. Without good torque control of the tip of the wire, physicians have difficulty steering the tip into the appropriate branches to reach the desired lesion.

In order to make a guide wire that meets the desired output requirement, a flexible section of the guide wire (typically the distal most 20 to 40 cm of the wire that will be inserted into the vasculature) can be created via grinding of the core wire to create the desired support and transition conditions. To improve compatibility with other devices that will be advanced over the guide wire, a covering is often placed over the ground section of the core wire and coated with a lubricious coating to improve lubricity. Flexible coverings can include one or more coils, tubes, and/or tubes with integrated spiral coil support. The flexible coverings can be aligned to adjacent components of the guide wire and locked into place at each end via adhesive or solder. These types of flexible coverings are typically attached to the core wire in only two places, at the proximal and distal ends of the flexible covering. In that regard, a rigid adhesive is often used to fixedly secure the ends of the flexible covering to the core wire. The lubricious coatings that are applied to these coverings provide excellent movement in an axial direction within the vasculature and also help devices move smoothly over the wire. However, the use of traditional flexible coverings has a significant deficiency relating to torqueing the tip of the guide wire when the distal section of the guide wire, including the flexible covering, is in tortuosity. In that regard, the more tortuosity that the flexible covering is pushed into and/or the more acute the tortuosity becomes, the more the torqueability of the guide wire tip is degraded.

This degradation in torqueability of the distal section of the guide wire relative to the proximal section of the guide wire occurs because the flexible coverings have very poor torqueability characteristics. For example, when the distal section of the guide wire is in significant tortuosity, as the proximal end of the wire is rotated, the torque is poorly transmitted to the tip from the core wire through the flexible covering because the flexible covering is typically only attached at each end. This results in the guide wire building up torque with the tip rotation lagging behind the proximal rotation. When the flexible covering is only locked at its ends, the core wire is rotating against a non-lubricious inner surface of the flexible covering and, therefore, not getting the benefit of the lubricity of the outer coating of the flexible covering. At some point, the torque builds up enough to overcome the tortuosity effect on the flexible covering and the flexible covering suddenly spins causing the distal tip of the guide wire to whip through a large angle quickly. This whipping of the distal tip worsens with severe tortuosity and/or increased length of tortuosity. The unwanted whipping of the distal tip can cause problems with placing the guide wire in the desired location within the patient's anatomy and, in severe cases, can even cause damage to the patient's anatomy.

Further, the use of a flexible covering can require a decrease in the diameter of the core to allow sufficient room for the flexible covering while maintaining the overall desired outer diameter of the intravascular device. Also, communication lines may extend along the length of the intravascular device between the flexible covering and the core such that the inner diameter of the flexible covering and outer diameter of the core must be within desired tolerances to ensure there is sufficient space for the communication lines. Assembly of such devices can be complicated and require multiple intricate assembly steps.

Accordingly, there remains a need for intravascular devices, systems, and methods that include one or more electronic, optical, or electro-optical components and have improved handling characteristics.

SUMMARY

The present disclosure is directed to intravascular devices, systems, and methods that include a guide wire having a polymer jacket applied over communication lines and a core member, where the communication lines have been wrapped around the core member.

For example, in some implementations a sensing guide wire is provided that includes a proximal portion and a distal portion, the distal portion including: a core member; a plurality of communication lines wrapped around the core member; a polymer jacket formed around the core member and the plurality of communication lines; and a sensing element positioned distal of the polymer jacket and communicatively coupled to the plurality of communication lines. The sensing element can be a pressure sensor, a flow sensor, or include both a pressure sensor and flow sensor. The communication lines can include electrical conductors and/or optical fibers. In some instances, the communication lines are electrical conductors having a diameter of 40 AWG or smaller. The plurality of communication lines can include between two and ten communication lines. In some particular embodiments, the plurality of electrical conductors consists of three conductors. The plurality of communication lines are wrapped around the core member with a pitch between about 0.25 mm and about 1,000 mm with a preferable pitch being between 3 mm and 5 mm. In other instances, the communication lines extend linearly along the core (e.g., parallel to the core) instead of being wrapped around the core. The plurality of communication lines can be communicatively coupled to a plurality of communication lines extending along the proximal portion of the guide wire.

In some instances, the polymer jacket includes at least one portion embedded with radiopaque material to define a radiopaque marker element. Further, a radiopaque marker element can be positioned around the core member such that the polymer jacket is formed around the radiopaque marker element. The polymer jacket can extend a full length of the core member or along only a portion of the core member. The polymer jacket can be formed of a polymer selected from the group of polymers consisting of polyurethanes, pebax, nylon, and/or combinations thereof. The polymer jacket can have an outer diameter of approximately 0.014", approximately 0.018", approximately 0.035", or other desired size.

In some embodiments, a method of forming a sensing guide wire is provided that includes communicatively coupling a plurality of communication lines to a sensing element; wrapping the plurality of communication lines around a core member; and forming a polymer jacket around the core member and the plurality of communication lines. The sensing element can be a pressure sensor, a flow sensor, or include both a pressure sensor and flow sensor. The communication lines can include electrical conductors and/or optical fibers. In some instances, the communication lines are electrical conductors having a diameter of 40 AWG or smaller. The plurality of communication lines can include between two and ten communication lines. In some particular embodiments, the plurality of electrical conductors consists of three conductors. The plurality of communication lines are wrapped around the core member with a pitch between about 0.25 mm and about 1,000 mm with a preferable pitch being between 3 mm and 5 mm. The plurality of communication lines can be communicatively coupled to a plurality of communication lines of a proximal portion of the guide wire.

In some instances, the method includes embedding at least a portion of the polymer jacket with radiopaque material to define a radiopaque marker element. In some implementations, the method includes positioning a radiopaque marker element around the core member. In that regard, forming the polymer jacket can include forming the polymer jacket around the radiopaque marker element. The polymer jacket can be formed to extend a full length of the core member or along only a portion of the core member. The polymer jacket can be formed of a polymer selected from the group of polymers consisting of polyurethanes, pebax, nylon, and/or combinations thereof. The polymer jacket can be formed to have an outer diameter of approximately 0.014", approximately 0.018", approximately 0.035", or other desired size.

In some instances, the plurality of communication lines are wrapped around the core member prior to forming the polymer jacket. In other instances, the plurality of communication lines are wrapped around the core member at the same time as forming the polymer jacket. Forming the polymer jacket can include moving the core member and the plurality of communication lines through a chamber containing a polymer. In some embodiments, an opening adjacent to the chamber can have an outer diameter approximately equal to a desired outer diameter of the polymer jacket. In other instances, forming the polymer jacket can include moving a chamber containing a polymer over the core member and the plurality of communication lines. In such an approach an opening adjacent to the chamber can have an outer diameter approximately equal to a desired outer diameter of the polymer jacket.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

Collectively.

FIG. 4 is a diagrammatic, schematic side view of a distal portion of an intravascular device showing an initial stage of communication lines being wrapped around a core according to the present disclosure.

FIG. 5 is a diagrammatic, schematic side view of the distal portion of the intravascular device of FIG. 4 showing an intermediate stage of communication lines being wrapped around a core according to the present disclosure.

FIG. 6 is a diagrammatic, schematic side view of the distal portion of the intravascular device of FIGS. 4 and 5 showing a final stage of communication lines being wrapped around a core according to the present disclosure.

FIG. 7 is a diagrammatic, schematic side view of the distal portion of the intravascular device of FIGS. 4-6 showing the communication lines wrapped around the core according to the present disclosure.

FIG. 8 is a diagrammatic, schematic side view of the distal portion of the intravascular device of FIGS. 4-7 showing an initial stage of applying a polymer jacket around the communication lines and the core according to the present disclosure.

FIG. 9 is a diagrammatic, schematic side view of the distal portion of the intravascular device of FIGS. 4-8 showing an intermediate stage of applying the polymer jacket around the communication lines and the core according to the present disclosure.

FIG. 10 is a diagrammatic, schematic side view of the distal portion of the intravascular device of FIGS. 4-9 showing a final stage of applying the polymer jacket around the communication lines and the core according to the present disclosure.

FIG. 11 is a diagrammatic, schematic side view of the distal portion of the intravascular device of FIGS. 4-9 showing a final stage of applying the polymer jacket around the communication lines and the core according to the present disclosure.

Collectively.

FIG. 12 is a diagrammatic, schematic side view of a distal portion of an intravascular device showing an initial stage of communication lines being wrapped around a core with application of a polymer jacket according to the present disclosure.

FIG. 13 is a diagrammatic, schematic side view of the distal portion of the intravascular device of FIG. 12 showing an intermediate stage of communication lines being wrapped around the core with application of the polymer jacket according to the present disclosure.

FIG. 14 is a diagrammatic, schematic side view of the distal portion of the intravascular device of FIGS. 12 and 13 showing a final stage of communication lines being wrapped around the core with application of the polymer jacket according to the present disclosure.

DETAILED DESCRIPTION

Figure 1:
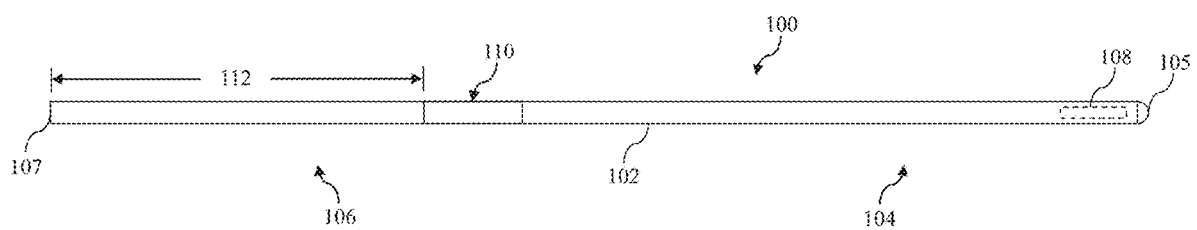
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal tip 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In some embodiments the electrical conductors are embedded within a core of the flexible elongate member. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In some instances, at least one of the electrical conductors and/or optical pathways is embedded within the core of the flexible elongate member 102, as described in U.S. Provisional Patent Application No. 61/935,113, filed Feb. 3, 2014, which is hereby incorporated by reference in its entirety. Generally, any number of electrical conductors, optical pathways, and/or combinations thereof can extend along the length of the flexible elongate member 102 between the connector 110 and the component 108, embedded in the core or not. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define component 108 to provide such functionality.

Figure 2:
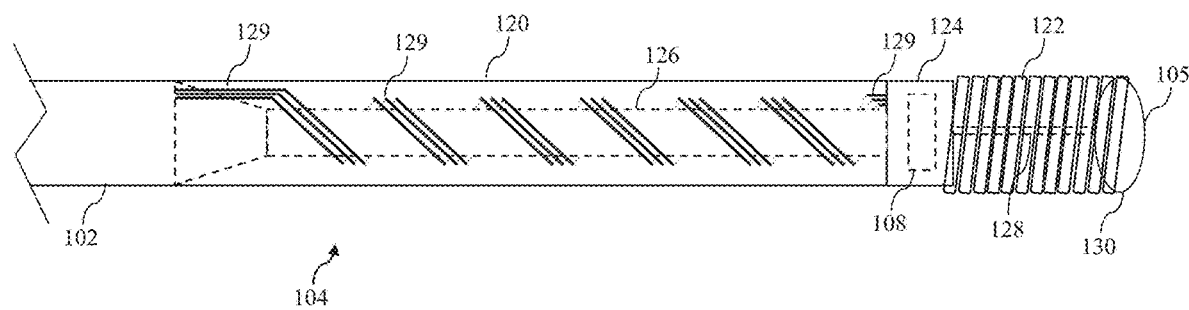
FIG. 2 is a diagrammatic, schematic side view of a distal portion of the intravascular device of FIG. 1 according to an embodiment of the present disclosure.
Figure 3:
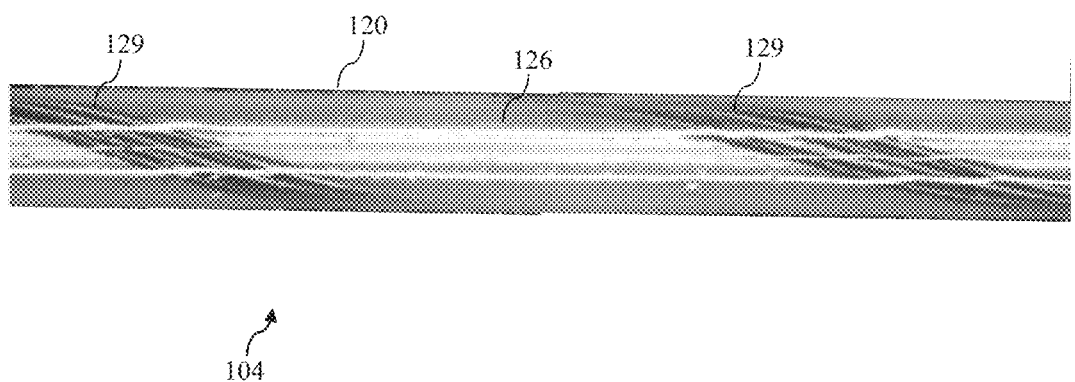
FIG. 3 is a photographic side view of a distal portion of the intravascular device according to an embodiment of the present disclosure.

Referring now to FIGS. 2 and 3, shown therein are aspects of the intravascular devices of the present disclosure that include a polymer jacket applied over communication lines and a core, where the communication lines have been wrapped around the core. In that regard, one of the major issues associated with existing functional guide wires is poor mechanical performance as compared to frontline guide wires. By forming a polymer jacket directly over the communication lines and core wire (as opposed to attaching a pre-formed polymer tubing over the communication lines and core wire), the polymer jacket has strong adhesion to the core wire along the entire length of the polymer jacket, which increases the transmission of torque from the core to the polymer jacket. Further, because the polymer jacket can have a smaller cross-sectional thickness as compared to existing flexible coverings (e.g., coils, polymer tubing, etc.), the diameter of the core can be increased. Increasing the diameter of the core can increase structural support and/or torqueability. As a result, intravascular devices utilizing the polymer jacket approaches in accordance with the present disclosure have been found to have significantly improved mechanical performance. In particular, the torque response of the distal portion of the guide wire is significantly improved as compared to existing sensing guide wires.

Referring now to FIG. 2, shown therein is a diagrammatic, schematic side view of the distal portion 104 of the intravascular device 100 according to an embodiment of the present disclosure. As shown, the distal portion 104 includes a proximal flexible element 120 and a distal flexible element 122 on each side of a housing 124 containing component 108. A core member 126 extends through the proximal flexible element 120. Similarly, a core member 128 extends through the distal flexible element 122. In some implementations, the core members 126 and 128 are an integral component (i.e., the core member 126 extends through the housing 124 and to define core member 128). Generally, the core members 126, 128 are sized, shaped, and/or formed out of particular material(s) to create a desired mechanical performance for the distal portion 104 of the intravascular device 100. In that regard, in some instances the core member 128 is coupled to a shaping ribbon. For example, in some particular implementations the core member 128 is coupled to a shaping ribbon utilizing a multi-flat transition as described in U.S. Provisional Patent Application No. 62/027,556, filed Jul. 22, 2014, which is hereby incorporated by reference in its entirety.

Generally, the proximal and distal flexible elements 120, 122 can include any suitable flexible elements, including coils, polymer tubes, and/or coil-embedded polymer tubes, but in accordance with the present disclosure at least a portion of the proximal flexible element 120 is defined by a polymer jacket. As discussed below, the polymer jacket is formed directly around the core member 126 and communication lines 129, which are wrapped around the core member 126. FIG. 3 provides an image of a distal portion 104 of an intravascular device 100 showing the polymer jacket 120 formed around communication lines 129 that are spiral wrapped around the core member 126.

A solder ball 130 or other suitable element is secured to the distal end of the distal flexible element 122. As shown, the solder ball 130 defines the distal tip 105 of the intravascular device 100 with an atraumatic tip suitable for advancement through patient vessels, such as vasculature. In some embodiments, a flow sensor is positioned at the distal tip 105 instead of the solder ball 130.

The distal portion 104 of the intravascular device 100—as well as the proximal portion 106 and the flexible elongate member 102—may be formed using any suitable approach so long as the proximal flexible element 122 includes a polymer jacket formed around the communication lines and core in accordance with the present disclosure. Accordingly, in some implementations the intravascular device 100 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013, U.S. patent application Ser. No. 14/135,117, filed Dec. 19, 2013, U.S. patent application Ser. No. 14/137,364, filed Dec. 20, 2013, U.S. patent application Ser. No. 14/139,543, filed Dec. 23, 2013, U.S. patent application Ser. No. 14/143,304, filed Dec. 30, 2013, and U.S. Provisional Patent Application No. 61/935,113, filed Feb. 3, 2014, each of which is hereby incorporated by reference in its entirety.

In some instances, a method of forming or manufacturing a sensing guide wire in accordance with the present disclosure includes providing the requisite components and coupling them together in a manner to form the intravascular device 100. In that regard, the communication lines 129 can be wrapped around the core member 126 and the polymer jacket can be applied before and/or after coupling other components together. In some instances, the distal portion 104 of the intravascular device 100 is formed as a sub-assembly that is then coupled to more proximal portions, such as the flexible elongate member 102 and/or the proximal portion 106. It is understood that the methods of forming or manufacturing a sensing guide wire in accordance with the present disclosure are exemplary and do not limit the manner in which the devices of the present disclosure can be made.

Figure 4:
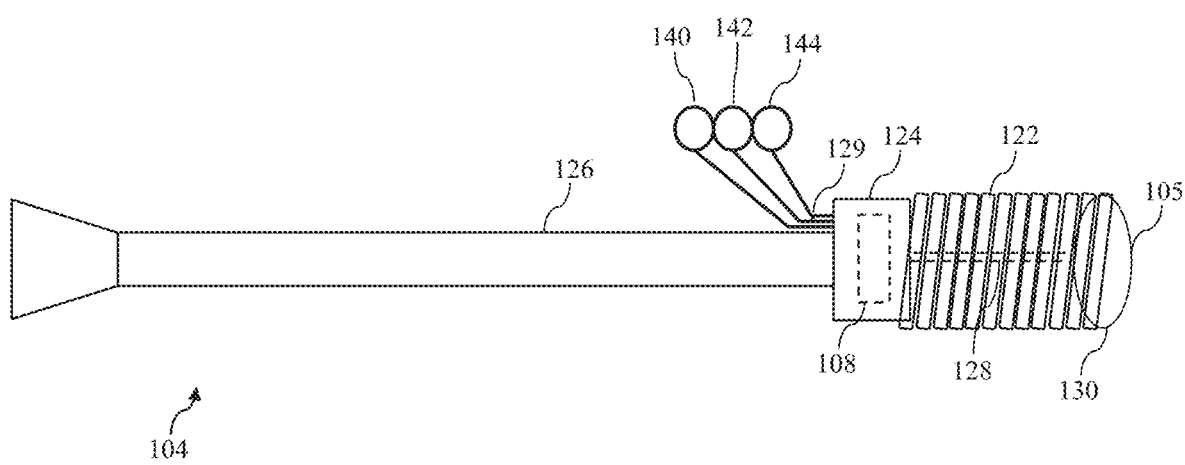
FIGS. 4-11 illustrate aspects of methods of manufacturing an intravascular device according to the present disclosure.

Collectively, FIGS. 4-11 illustrate aspects of methods of manufacturing an intravascular device according to the present disclosure, such as the intravascular devices shown in FIGS. 1-3 and described above. Referring initially to FIG. 4, communication lines 129 have been communicatively coupled to the sensing element 108. In this regard, the type of connection is dependent upon the type(s) of communication lines 129 utilized. For example, for electrical conductors a suitable electrical connection (e.g., solder, wire bonding, etc.) may be used, while for optical fibers a suitable optical connection may be used.

With the communication lines 129 coupled to the sensing element, the communication lines 129 can be wrapped around the core member 126. It is understood, however, that in other implementations that the communication lines 129 may be wrapped around the core member 126 prior to being coupled to the sensing element 108. Further, in yet other instances, the communication lines extend linearly along the core (e.g., parallel to the core) instead of being wrapped around the core. In the illustrated embodiment, three communication lines 129 are shown with corresponding supplies of communication line 140, 142, 144. In some instances, the supplies of communication line 140, 142, 144 are utilized to keep the communication lines 129 organized during the wrapping process. For example, in some instances the supplies of communication line 140, 142, 144 are spools of wire, cable, fiber, etc. that provide a predictive supply of communication line for wrapping around the core member 126. In some implementations, smaller gauge electrical conductors (e.g., 40 gauge to 60 gauge, with a preference of 48 to 50 gauge) are utilized to provide more uniform wrapping of the communication lines 129 around the core member 126 and/or more uniform application of polymer to the core member 126 wrapped with the communication lines 129. Further, electrical conductors with higher tensile lead materials, such as CS-95, can be utilized to minimize breakage during manufacturing and/or use of the device.

Figure 5:
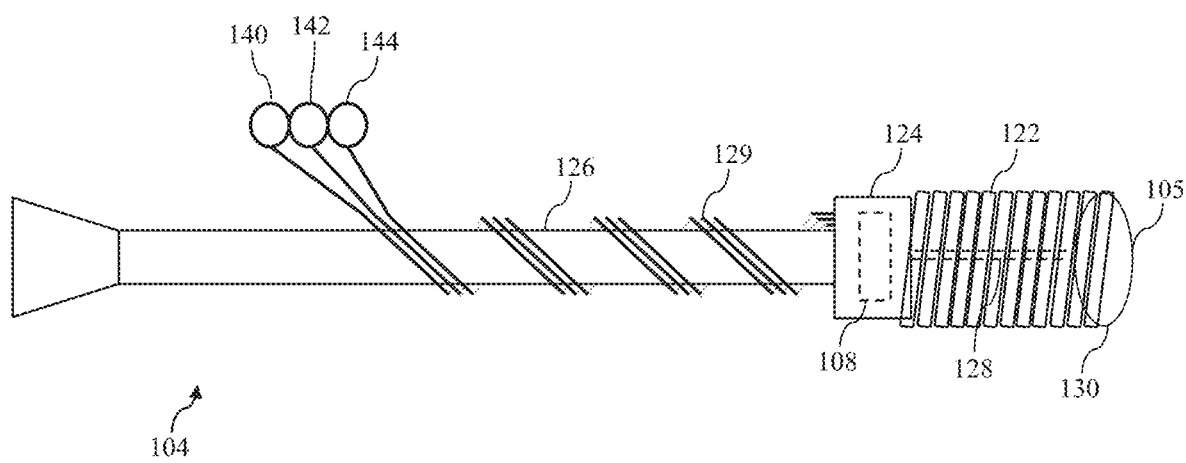
Figure 6:
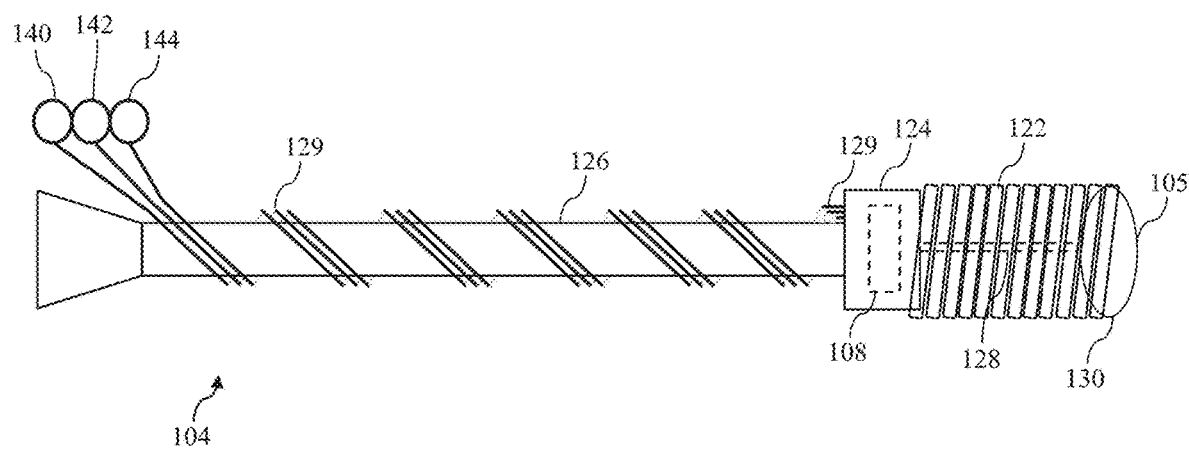

Generally, the communication lines 129 can be wrapped around the core member 126 by rotating and translating the core member 126 relative to the supplies of communication line 140, 142, 144. In this regard, the speeds of rotation and translation can be selected to achieve a desired pitch of the wrapped communication lines 129. In some instances, the pitch of the wrapped communication lines 129 is between about 0.25 mm and about 1,000 mm with a preferable pitch being between 3 mm and 5 mm. Alternatively, the communication lines 129 can be wrapped around the core member 126 by rotating and translating the supplies of communication line 140, 142, 144 around the core member 126. Again, the speeds of rotation and translation can be selected to achieve a desired pitch of the wrapped communication lines 129. FIGS. 4-6 are representative of both approaches of wrapping the communication lines 129. In particular, FIG. 4 shows an initial stage of wrapping, FIG. 5 shows an intermediate stage of wrapping, and FIG. 6 shows a final stage of wrapping.

Figure 7:
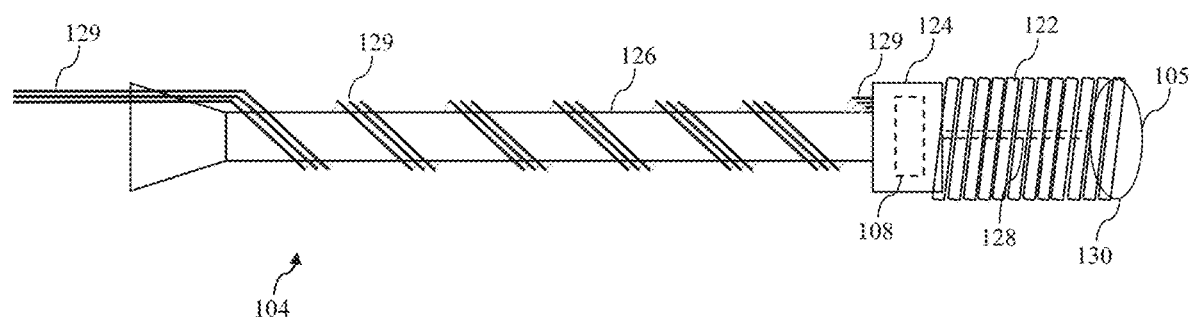

In this regard, while FIG. 6 shows the communication lines 129 wrapped around the core member, the proximal ends of the communication lines 129 are still attached to the supplies of communication line 140, 142, 144. Accordingly, with the wrapping complete each of the communication lines 129 will be separated (e.g., cut) from the supplies of communication line 140, 142, 144. In this regard, enough communication line 129 needs to be provided to allow each of the communication lines 129 to be coupled to a communication line of a proximal portion of the guide wire such that signals can be transmitted along the length of the guide wire between the sensing element 108 and the connector 110. FIG. 7 illustrates such extensions of the communication lines 129 extending proximal of the core member 126. These extensions of the communication lines 129 can be cut to a more specific length when actually coupled to the proximal communication lines.

In some instances, the communication lines 129 are maintained in the wrapped configuration prior to application of the polymer jacket 120 through use of a mechanical holder (e.g., clamp or other device for applying pressure to hold the communication lines in place), adhesive (e.g., using an adhesive at various points along the length of the communication lines to provide anchor points until the polymer jacket is applied), or shrink tubing applied at appropriate points, maintaining the communication lines in tension, and/or combinations thereof.

Figure 8:
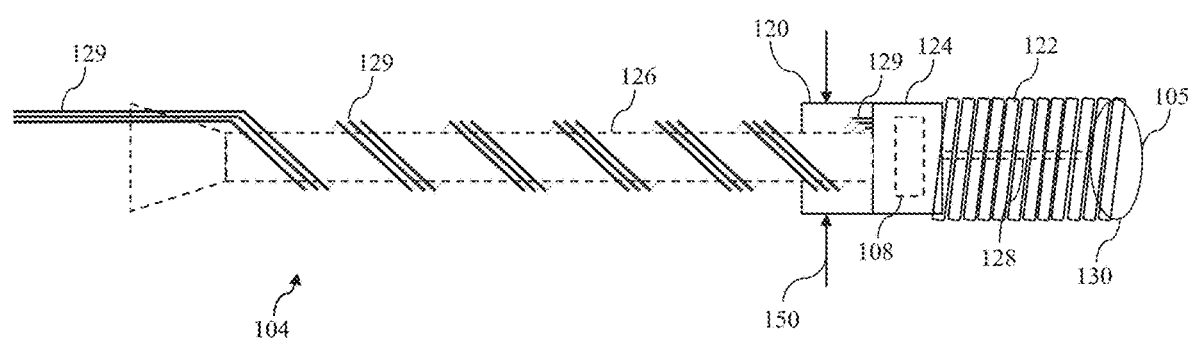
Figure 9:
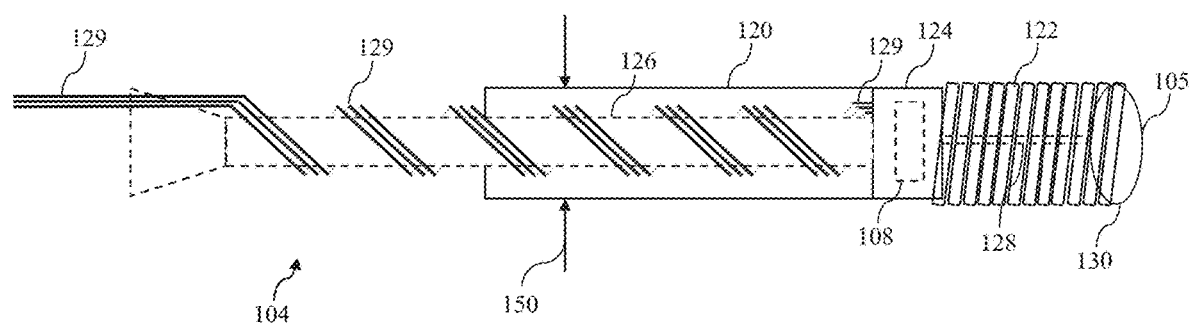
Figure 10:
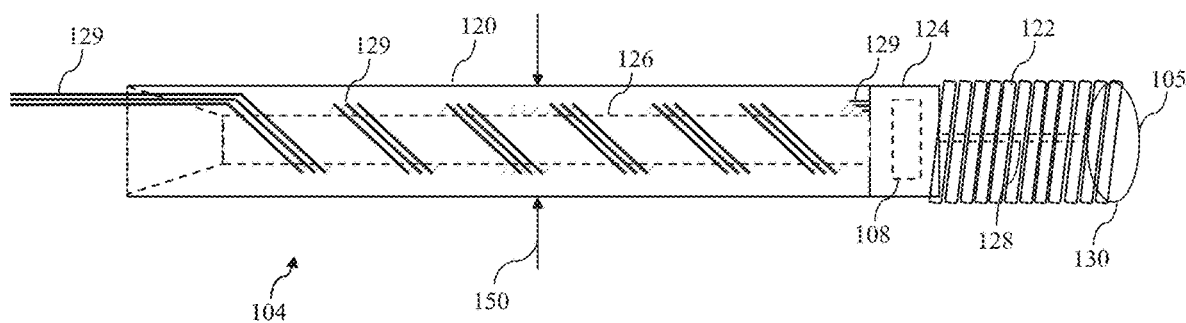

With the communication lines 129 wrapped around the core member 126, the polymer jacket 120 can be formed around the communication lines 129 and core member 126. In this regard, FIGS. 8-10 show the polymer jacket 120 being formed. In particular, FIG. 8 shows an initial stage of the polymer jacket being formed, FIG. 9 shows an intermediate stage, and FIG. 10 shows a final stage.

Generally, the polymer jacket 120 can be formed using any suitable means, including molding, extruding, and/or combinations thereof. For example, in some implementations the core member 126 wrapped with the communication lines 129 can be placed in a mold and a polymer can be injected into the mold to form the polymer jacket 120. In some implementations, the core member 126 with the wrapped communication lines 129 is moved relative to a chamber containing the polymer. For example, the core member 126 with the wrapped communication lines 129 can be pulled (or pushed) through the chamber containing the polymer such that the polymer is applied along the length of the core member 126 to define the polymer jacket 120. Alternatively, the chamber containing the polymer can be moved over the core member 126 wrapped with the plurality of communication lines 129, while maintaining the core member 126 stationary. The chamber can have a pressurized supply of polymer to ensure that an adequate supply of polymer is always present for coating the core member 126 to form the polymer jacket. In some instances, an opening adjacent to the chamber (e.g., an exit of the chamber or a separate component adjacent the exit of the chamber) has an outer diameter approximately equal to the desired outer diameter of the polymer jacket. In this regard, as the core member 126 with the polymer applied from the chamber passes through the opening, the excess polymer extending beyond the desired diameter can be removed by contact with the boundary of the opening.

The polymer jacket 120 protects the communication lines 129 from damage during use, while maintaining flexibility of the intravascular device 100. Therefore, the polymer utilized must be durable, flexible, and biocompatible. Accordingly, the polymer jacket 120 can be formed of any suitable material or combination of materials, including without limitation pellethane, other polyurethanes, nylon, pebax or other thermoplastics of suitable flexibility, and/or combinations thereof. Also, in some embodiments the polymer jacket 120 is coated with a lubricious hydrophilic coating.

As shown in FIGS. 8-10, the polymer jacket 120 can be formed to have a substantially uniform outer diameter 150 despite the lack of uniformity in diameter resulting from wrapping the communication lines 129 around the core member. Generally, the diameter 150 is approximately equal to the maximum desired outer diameter of the intravascular device 100. Accordingly, in some particular implementations the diameter 150 is about 0.014", 0.018", or 0.035". In some implementations, the outer diameter is achieved by passing the core member 126 with the polymer applied thereto through an opening having the desired outer diameter, machining/laser ablating/cutting or otherwise processing the applied polymer to achieve the desired outer diameter, and/or combinations thereof.

In some instances, the polymer jacket 120 extends the entire length of the core member 126 positioned proximal of the sensing element 108. In this regard, in some instances the polymer jacket 120 will abut a corresponding outer member of the flexible elongate member 102 or other component of the guide wire 100, which will typically have the same outer diameter as the polymer jacket 120.

Figure 11:
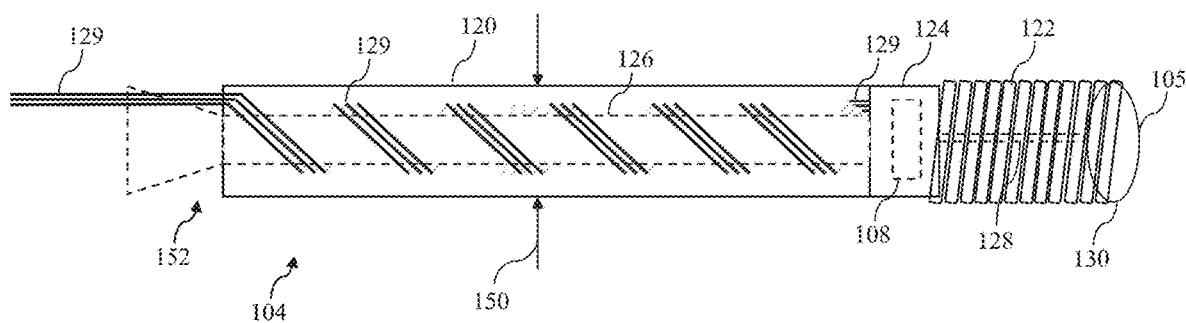

In some implementations, the polymer jacket 120 extends only a portion of the length of the core member 126 positioned proximal of the sensing element 108. For example, FIG. 11 shows an embodiment where the polymer jacket 120 extends only a portion of the length of the core member 126 such that a proximal section 152 of the core member 126 is exposed. In such instances, the polymer jacket 120 may be formed to have the desired length to expose the proximal section 152 or a portion of the polymer initially applied to the core member 126 may be removed to expose the proximal section 152. In this regard, it may be desirable to have the polymer jacket 120 extend along only a portion of the core member to facilitate coupling to more proximal portions of the guide wire, such as flexible element 102 and/or proximal section 106. A similar approach may be utilized to facilitate coupling to distal portions of the guide wire as well (e.g., in embodiments where the communication lines 129 are coupled to the sensing element 108 after forming the polymer jacket 120). In some instances, the gap(s) between the polymer jacket 120 and the adjacent components of the guide wire are subsequently filled with a polymer, adhesive, and/or other suitable material(s) after coupling the core member 126 and/or the communication lines 129 to the adjacent proximal and/or distal component(s). In some particular instances, the gap(s) are filled with the same material(s) utilized to form the polymer jacket 120.

By forming the polymer jacket 120 directly around the communication lines 129 and core member 126 a strong mechanical coupling is provided along the entire length of the polymer jacket 120, which significantly increases the torque transfer as compared to the previous approaches that used coils, polymer tubes, and/or combinations thereof. Further, the wrapped communication lines 129 provide a symmetrical torque response that is predictable even when the guide wire is under tortuosity, especially when compared to the previous approaches that extended electrical conductors linearly along one side of the core that can cause significant whipping in tortuous conditions. Further, since the polymer jacket 120 does not have a constant thickness, but instead conforms to the shape of the communication lines 129 and the core member 126 while maintaining a uniform outer diameter, the space available for the core member and the communication lines can be maximized, which can provide improved handling performance by allowing the for the use of larger diameter core members. Further still, the polymer jacket 120 can eliminate the need for adhesives to connect coils and/or tubes to other components, while also eliminating the alignment issues associated with such connections. In this regard, the polymer jacket 120 can be applied such that it transitions smoothly to the housing 124 and/or the flexible elongate element 102. Finally, the use of a polymer jacket 120 in accordance with the present disclosure can reduce the cost and complexity of manufacturing, as the application of the polymer is reasonably fast, the polymer application system provides alignment of the polymer during the application process, and the cost of the polymer is minimal compared to more traditional coils or tubes that have to be manufactured and then assembled with adhesives.

Figure 12:
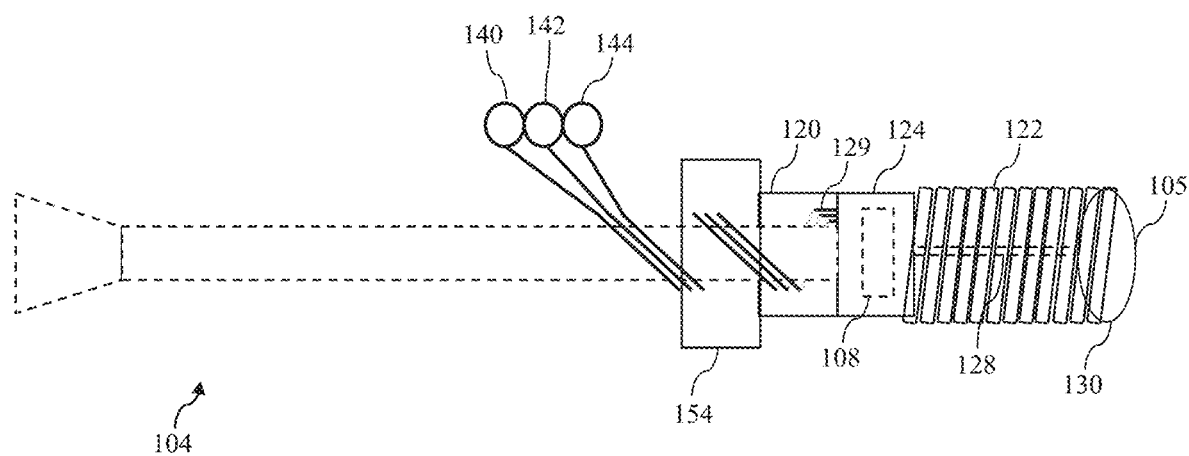
FIGS. 12-14 illustrate aspects of methods of manufacturing an intravascular device according to the present disclosure.
Figure 13:
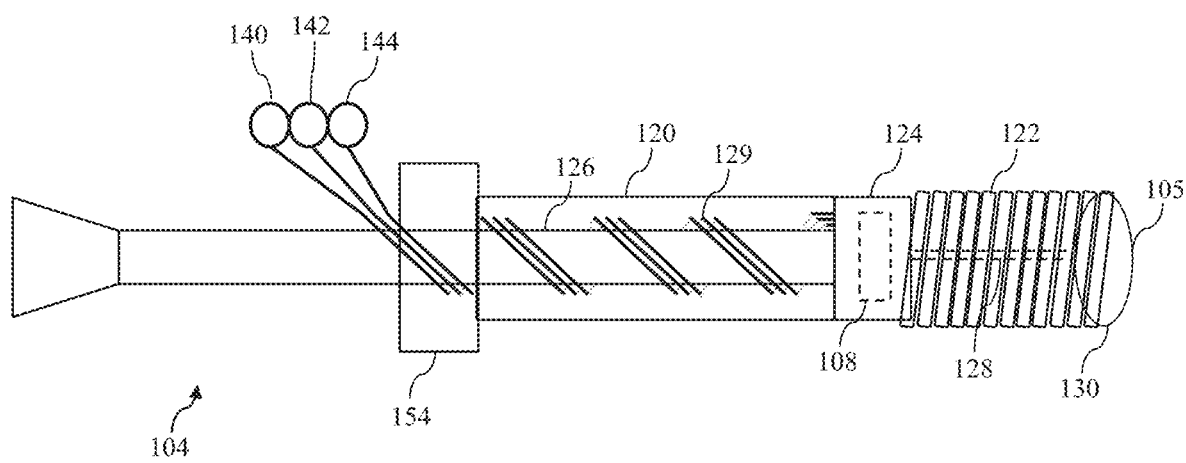
Figure 14:
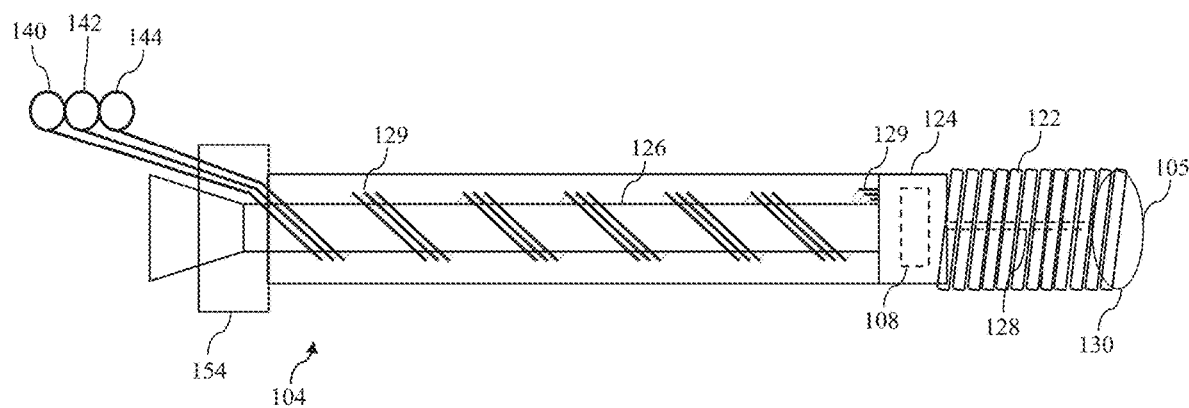

Collectively, FIGS. 12-14 illustrate aspects of methods of manufacturing an intravascular device according to the present disclosure, such as the intravascular devices shown in FIGS. 1-3 and described above. In this regard, whereas FIGS. 4-11 illustrated embodiments where the communication lines 129 were wrapped around the core member 126 prior to forming the polymer jacket 120, FIGS. 12-14 illustrate embodiments where the communication lines 129 are wrapped around the core member 126 at the same time as forming the polymer jacket 120. In particular, FIG. 12 shows an initial stage of wrapping the communication lines 129 and forming the polymer jacket, FIG. 13 shows an intermediate stage, and FIG. 14 shows a final stage.

In some implementations, the core member 126 is rotated and translated relative to the supplies of communication line 140, 142, 144 to wrap the communication lines 129 around the core member 126, while being simultaneously translated through a chamber 154 containing the polymer that is applied to the core member 126 and the wrapped communication lines 129. In other instances, the core member 126 is held stationary and the supplies of communication line 140, 142, 144 and the chamber 154 move relative to the core member 126 to wrap the communication lines 129 and form the polymer jacket 120.

Figure 15:
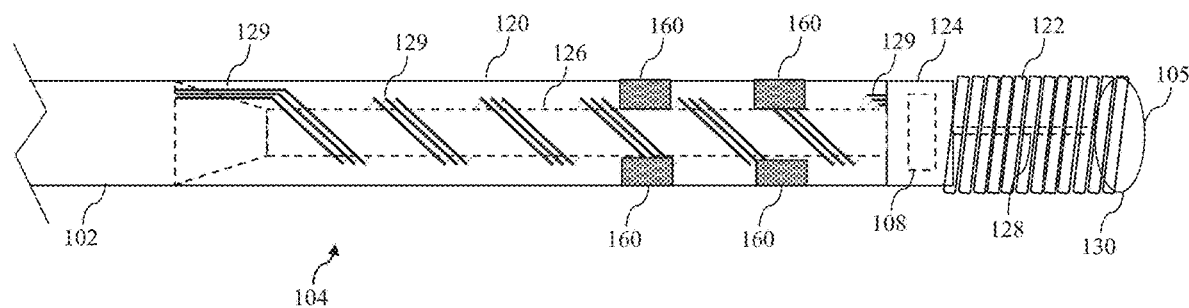
FIG. 15 is a diagrammatic, schematic side view of a distal portion of an intravascular device having radiopaque marker elements according to an embodiment of the present disclosure.
Figure 16:
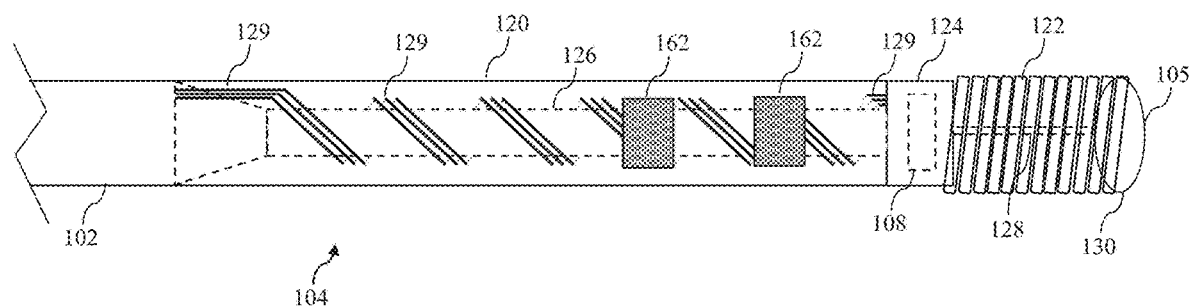
FIG. 16 is a diagrammatic, schematic side view of a distal portion of an intravascular device having radiopaque marker elements according to another embodiment of the present disclosure.

In some implementations, portions of the polymer jacket 120 are embedded with radiopaque material particles to create radiopaque marker elements. For example, as shown in FIG. 15, radiopaque marker elements 160 can be created by utilizing a polymer with embedded radiopaque material particles to form the polymer jacket 120 where the radiopaque marker elements are desired to be positioned. Similarly, the polymer material can be selectively embedded with radiopaque material particles as it is applied around the core member 126 and communication lines 129 at the locations where the radiopaque marker elements are desired to be positioned. As an alternative to embedding radiopaque material within the polymer, separate radiopaque marker elements 162 can be positioned around the core member 126 prior to application of the polymer jacket 120 as shown in FIG. 16. Though shown as being positioned over the communication lines 129 in FIG. 16, the radiopaque marker elements 162 can be under the wrapped communication lines 129 in other implementations. Since the polymer jacket 120 is formed with a consistent outer diameter regardless of the underlying structure, as described above, the outer diameter of the polymer jacket 120 can remain at the desired size even with the use of separate radiopaque marker elements 162.

The radiopaque marker elements 160, 162 allow co-registration of the location of the intravascular device 100 with other diagnostic techniques, such as external and internal imaging. For example, in some instances the radiopaque marker elements 160, 162 are utilized in combination with the housing 124 to define a pattern of radiopaque marker elements. For example, using the housing 124 and the radiopaque marker elements 160, 162 as markers and the non-radiopaque sections of the polymer jacket 120 as spacers, a repeating pattern of radiopaque markers with known spacings can be provided. Sensing guide wires having this radiopaque pattern can be utilized to identify the exact location of the sensing element based on the location of the radiopaque housing and marker elements. In some instances, the intravascular device can include a radiopaque patterned flexible tip as described in U.S. Provisional Patent Application No. 62/074,320, filed Nov. 3, 2014 and titled "INTRAVASCULAR DEVICES, SYSTEMS, AND METHODS HAVING A RADIOPAQUE PATTERNED FLEXIBLE TIP," which is hereby incorporated by reference in its entirety.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular pressure-sensing guide wire, comprising:
   a proximal portion and a distal portion configured to be positioned within a blood vessel, the distal portion including:
   a core wire;
   a plurality of communication lines extending along the core wire, wherein at least a portion of the plurality of communication lines is wrapped around the core wire and directly contacts the core wire;
   a polymer jacket formed around the core wire and the plurality of communication lines such that the polymer jacket directly contacts the plurality of communication lines and the core wire while maintaining a substantially uniform outer profile having an outer diameter between about 0.010" and about 0.040", wherein the polymer jacket comprises a first portion of a length of the distal portion;
   a pressure-sensing element configured to sense a pressure within the blood vessel, wherein the pressure-sensing element is disposed distal of the polymer jacket and communicatively coupled to the plurality of communication lines, wherein the plurality of communication lines are configured to transmit signals associated with the pressure-sensing element; and
   a coil configured to provide flexibility for the distal portion during positioning within the blood vessel, wherein the coil is different than the plurality of communication lines, and wherein the coil comprises a different, second portion of the length of the distal portion.

2. The intravascular pressure-sensing guide wire of claim 1, wherein the distal portion further comprises at least one of a flow sensor or an ultrasound transducer.

3. The intravascular pressure-sensing guide wire of claim 1, wherein a further portion of the plurality of communication lines extends linearly along the core wire.

4. The intravascular pressure-sensing guide wire of claim 1, wherein a majority of a length of the plurality of communication lines are wrapped around the core wire.

5. The intravascular pressure-sensing guide wire of claim 1, wherein the plurality of communication lines includes a plurality of electrical conductors.

6. The intravascular pressure-sensing guide wire of claim 5, wherein the plurality of electrical conductors have a diameter of 40 AWG or smaller.

7. The intravascular pressure-sensing guide wire of claim 6, wherein the plurality of electrical conductors consists of three conductors.

8. The intravascular pressure-sensing guide wire of claim 4, wherein the plurality of communication lines are wrapped around the core wire with a pitch between about 0.25 mm and about 1,000 mm.

9. The intravascular pressure-sensing guide wire of claim 1, wherein the plurality of communication lines are communicatively coupled to a plurality of communication lines extending along the proximal portion of the guide wire.

10. The intravascular pressure-sensing guide wire of claim 1, wherein the polymer jacket includes at least one portion embedded with radiopaque material to define a radiopaque marker element.

11. The intravascular pressure-sensing guide wire of claim 1, further comprising a radiopaque marker element positioned around the core wire such that the polymer jacket is formed around the radiopaque marker element.

12. The intravascular pressure-sensing guide wire of claim 1, wherein the polymer jacket extends a full length of the core wire.

13. The intravascular pressure-sensing guide wire of claim 1, wherein the polymer jacket extends along only a portion of the core wire.

14. The intravascular pressure-sensing guide wire of claim 1, wherein the polymer jacket is formed of a polymer selected from a group of thermoplastic polymers consisting of: polyurethane, pellethane, pebax, and nylon.

15. The intravascular pressure-sensing guide wire of claim 1, wherein the polymer jacket has an outer diameter of approximately 0.014", approximately 0.018", or approximately 0.035".

16. The intravascular pressure-sensing guide wire of claim 1, wherein the polymer jacket forms a mechanical coupling with the plurality of communication lines and the core wire.

17. The intravascular pressure-sensing guide wire of claim 16, wherein the plurality of communication lines are wrapped around the core wire to provide a symmetrical torque response.

18. A method of forming an intravascular pressure-sensing guide wire, the method comprising:
   communicatively coupling a plurality of communication lines to a pressure-sensing element configured to measure pressure within a blood vessel when the intravascular pressure-sensing guide wire is positioned within the blood vessel, wherein the plurality of communication lines are configured to transmit signals associated with the pressure-sensing element;
   extending the plurality of communication lines along a core wire such that at least a portion of the plurality of communication lines is wrapped around the core wire and directly contacts the core wire;
   forming a polymer jacket around the core wire and the plurality of communication lines such that the polymer jacket directly contacts the plurality of communication lines and the core wire while maintaining a substantially uniform outer profile having an outer diameter between about 0.010" and about 0.040", wherein the polymer jacket comprises a first portion of a length of a distal portion of the intravascular pressure-sensing guide wire; and
   providing a coil for flexibility of the distal portion during positioning within the blood vessel, wherein the coil is different than the plurality of communication lines, and wherein the coil comprises a different, second portion of the length of the distal portion.

19. The method of claim 18, wherein extending the plurality of communication lines along the core wire includes extending a further portion of the plurality of communication lines linearly along the core wire.

20. The method of claim 18, wherein extending the plurality of communication lines along the core wire includes wrapping a majority of a length of the plurality of communication lines around the core wire.

21. The method of claim 18, wherein forming the polymer jacket includes moving the core wire and the plurality of communication lines relative to a chamber containing a polymer.

22. The method of claim 21, wherein an opening adjacent to the chamber has an outer diameter approximately equal to a desired outer diameter of the polymer jacket.

\* \* \* \* \*